United States Patent [19]
Breyen et al.

[11] Patent Number: 5,411,545
[45] Date of Patent: May 2, 1995

[54] MEDICAL ELECTRICAL LEAD

[75] Inventors: Mark D. Breyen, Plymouth; Naim S. Istephanous, Roseville; Robert E. Kraska, Minneapolis; Joseph F. Lessar, Coon Rapids; Jennifer P. Miller, Elk River, all of Minn.

[73] Assignee: Medtronic, Inc., Minneapolis, Minn.

[21] Appl. No.: 212,476

[22] Filed: Mar. 14, 1994

[51] Int. Cl.⁶ .............................................. A61N 1/05
[52] U.S. Cl. .................................................... 607/122
[58] Field of Search ................ 607/115, 116, 121, 122, 607/123

[56] References Cited

U.S. PATENT DOCUMENTS

| | | | |
|---|---|---|---|
| 4,012,103 | 3/1977 | Lunquist | 339/111 |
| 4,338,947 | 7/1982 | Williams | 128/642 |
| 4,355,647 | 10/1982 | Heidjann et al. | 130/24 |
| 4,860,446 | 8/1989 | Lessar et al. | 29/858 |
| 4,947,866 | 8/1990 | Lessar et al. | 128/784 |
| 4,964,414 | 10/1990 | Handa et al. | 128/784 |
| 4,964,925 | 10/1990 | Hagenfeldt et al. | 148/325 |
| 5,040,544 | 8/1991 | Lessar et al. | 128/784 |
| 5,241,957 | 9/1993 | Camps et al. | 607/119 |

OTHER PUBLICATIONS

*A Guide To Cardiac Pacemakers,* Chapter 6–lead Atlas, by Victor Parsonnet, M.D. and Todd Rogers, 1983, pp. 349–443, Philadelphia P.a., F.A. Davis Co.

*Materials Aspects of Implantable Cardiac Pacemaker Leads,* Medical Progress Through Technology,, by Stephen D. Bruck & Edward P. Mueller, Martinus Nijhoff Publishers, Boston, 13:149–160 (1988).

*New Pacing Lead Conductors,* by J. E. Upton, Medtronic, Inc., Minnesota, published in World Symposium On Cardiac Pacing, 6th, Montreal, 1979. Cardiac Pacing-State of the Arts, 1979: Proceedings, Montreal Que.: PACESYMP, 1979 Chapter 29, pp. 6–9.

*Drawn Brazed Strand Conductors for Medtronic Pacing Leads,* by Jim Upton, Medtronic, Inc., 1981.

Primary Examiner—William E. Kamm
Assistant Examiner—Scott M. Getzow
Attorney, Agent, or Firm—Daniel W. Latham; Harold R. Patton

[57] ABSTRACT

A medical electrical lead of the type which includes an electrode at a distal end of the lead a connector at a proximal end of the lead and an elongated electrical conductor extending between the electrode and the connector. The conductor is comprised of a wire wound in a coil configuration with the wire comprised of a duplex stainless steel having a composition of at least 22% chromium, 3% molybdenum and 5% nickel. Material of such composition has been found to have suitable conductivity for use with implantable pulse generators and suitable fatigue strength when used in endocardial lead placement. Moreover, such material has been found to pass tests intended to detect metal ion oxidation (MIO) in polymeric materials.

6 Claims, 2 Drawing Sheets

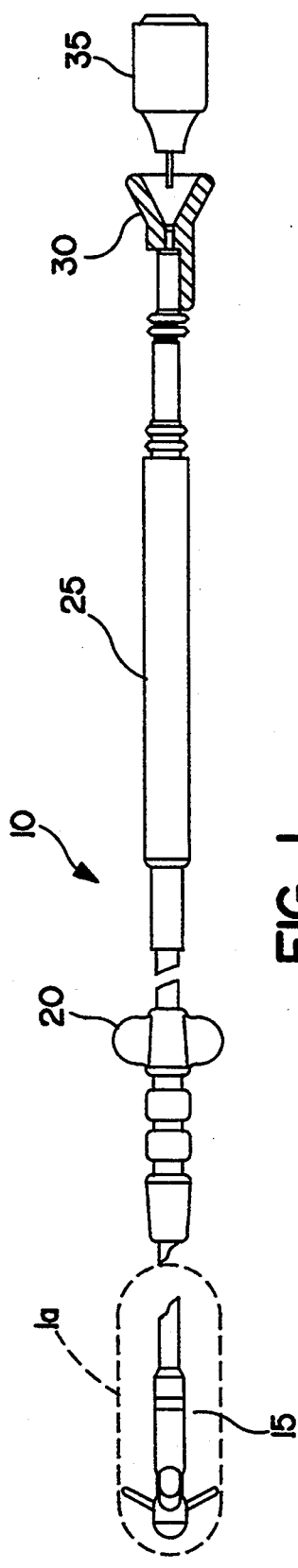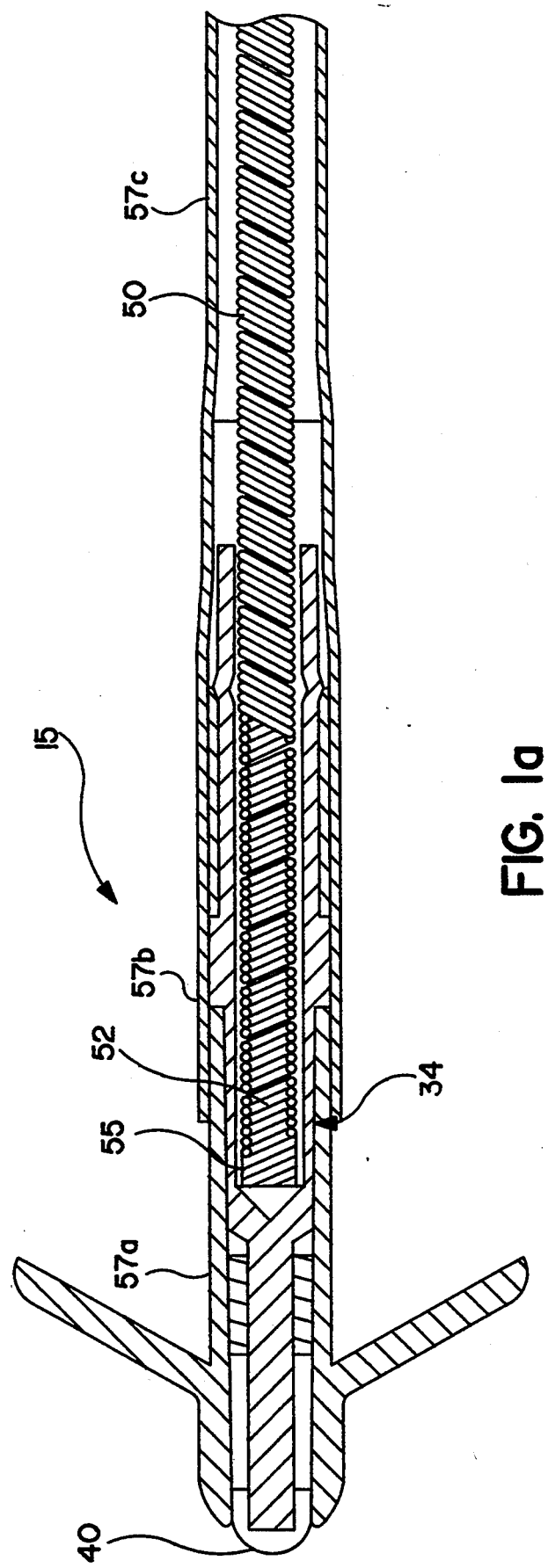
FIG. 1
FIG. 1a

MEDICAL ELECTRICAL LEAD

BACKGROUND OF THE INVENTION

The present invention relates to medical electrical leads and, in particular, to conductors for such leads.

Early cardiac pacemaker conductors were composed of numerous fine, stranded stainless steel wires. Marked improvement in both fracture rate and flexibility resulted when stainless steel conductors were wound into small coils with a hollow core. The hollow core of the coils also improved implantation since a stylet could be passed through the core during implantation to stiffen the lead. Corrosion resistance was significantly increased when stainless steel was replaced with more corrosion-resistant platinum-iridium and nickel alloys such as MP35N. Highly specialized conductors were used with such alloys such as the use of multifilar wire coils (to avoid loss of electrical continuity in the event that one wire breaks) and drawn brazed strand (DBS) wire (to provide a low electrical resistance in a wire of high fatigue strength). Multifilar coils can also be used in side-by-side or coaxial arrangements with insulation separating the conductors to provide individual conductors for the transmission of separate signals or stimulation pulses. However, it has been noted that polymeric materials (such as polyether urethanes) used for lead insulation can be adversely affected over long periods of implantation by metal ions from the nickel alloy conductors. Accordingly, it would be desirable to replace nickel alloy conductors like MP35N with other conductors which would not exhibit such a problem.

Of critical importance in this effort is to find a wire material that can be used in a multifilar coil wire geometry that will not fail under the mechanical stresses to which the lead will be subjected. The motions an implanted lead can experience are tension, twist and bending within the coil wire. Each of these produce either normal (tensile or compressive) or shear stresses which occur in all directions, but certain directions predominate depending on the modes of motion involved. If the magnitude of these stresses are too great with respect to the fatigue strength of the material, the structure will fail. Also of great importance is to find a wire material that will provide low electrical resistance.

It is therefore an object of the invention to provide a medical electrical lead having a conductor material that will not promote the degradation of adjacent polymeric materials.

It is also an object of the invention to provide a medical electrical lead having a conductor material with good fatigue strength when used in a coil geometry.

It is also an object of the invention to provide a medical electrical lead having a conductor material with low electrical resistance.

SUMMARY OF THE INVENTION

These and other objects are accomplished by the medical electrical lead of the present invention. We have discovered a medical electrical lead of the type which includes an electrode at a distal end of the lead a connector at a proximal end of the lead and an elongated electrical conductor extending between the electrode and the connector. The conductor is comprised of a wire wound in a coil configuration with the wire comprised of a duplex stainless steel having a composition of at least 22% chromium, 3% molybdenum and 5% nickel. Material of such composition and structure has been found to have suitable conductivity for use with implantable pulse generators or neurostimulators and suitable fatigue strength when used in endocardial lead placement. If additional conductivity is required, such as for use with an implantable defibrillator, the duplex stainless steel can also be provided with a core of silver or some other more conductive material in the same manner as conventional drawn brazed strand (DBS) wire. Moreover, such material has been found to pass tests intended to detect metal ion oxidation (MIO) in polymeric materials.

BRIEF DESCRIPTION OF THE DRAWINGS

FIG. 1 is a plan view of a medical electrical lead system suitable for endocardial stimulation by an implantable heart pacemaker.

FIG. 1a is a cross-sectional view of a lead assembly portion of the lead system of FIG. 1.

DETAILED DESCRIPTION OF THE INVENTION

In a preferred embodiment of the present invention, a medical electrical lead comprises an electrode at a distal end thereof, a connector at a proximal end thereof and an elongated electrical conductor extending between the electrode and the connector, the conductor in electrical contact with the electrode at a distal end and in electrical contact with the connector at a proximal end, the conductor comprised of a plurality of wires wound in a multifilar coil configuration, the wire comprised of a duplex stainless steel.

By duplex stainless steel, we mean a stainless steel having a ferritic-austenitic microstructure and a composition which includes percentages of austenitic phase stabilizers (e.g. nickel (Ni), manganese (Mn), copper (Cu), carbon (C), or nitrogen (N)) and ferrite phase stabilizers (e.g. chromium (Cr), molybdenum (Mo), silicon (Si), or niobium (Nb)) and appropriate thermomechanical treatments such that both the austenitic and ferritic structures are present at room temperature. The particular duplex stainless steels used in the present invention include those which include higher levels of chromiun, molybdenum and nickel (and also nitrogen) than conventional duplex stainless steels. Suitable duplex stainless steels according to the present invention are therefore those duplex stainless steels containing at least about 22% chromium, 3% molybdenum and 5% nickel. One such material is taught in European Patent Application 0 339 004 "Use of a Stainless Steel Alloy as Material for Medical Implant" which is incorporated herein by reference in its entirety. That patent application teaches a material having a composition which can be stated to be nominally Fe—25Cr—7Ni—4Mo—0.3N (commercially available as Sandvik alloy SAF2507).

The duplex alloys used in the present invention should be cold drawn through diamond dies with inert atmosphere annealing (e.g. argon atmosphere) between draws in order to limit the introduction of impurities. A fully cold worked or "full hard" condition for the wire gives the wire the best mechanical properties and does not significantly affect corrosion performance.

The wire in medical lead applications is typically made in round diameters ranging from about 0.004 to 0.010 although wire diameters as small as 0.001 can be used. The wire should be chemically cleaned in a conventional manner after the final draw to remove surface impurities. Final chemical cleaning is typically undertaken by methods which are conventional for removing organic lubricants from stainless steel wire surfaces.

A smooth surface finish for the wire is desirable since a smooth surface is easier to clean, and presents a shiny metallic finish that is aesthetically pleasing. Such a finish is readily achieved with the duplex alloy used in the present invention.

Figure 2A:
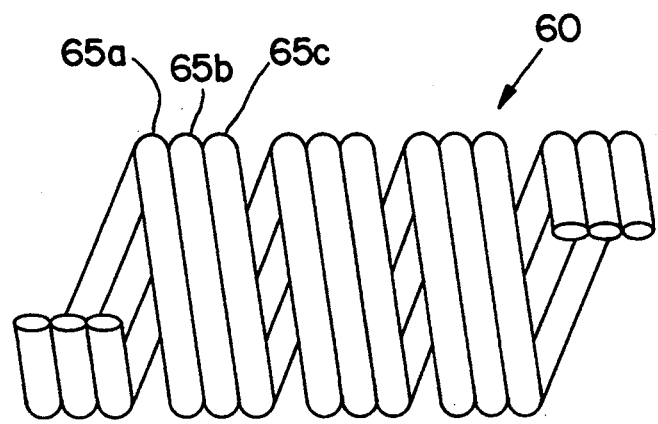
FIG. 2a is a side elevational view of a trifilar conductor winding for use in a lead conductor.
Figure 2B:
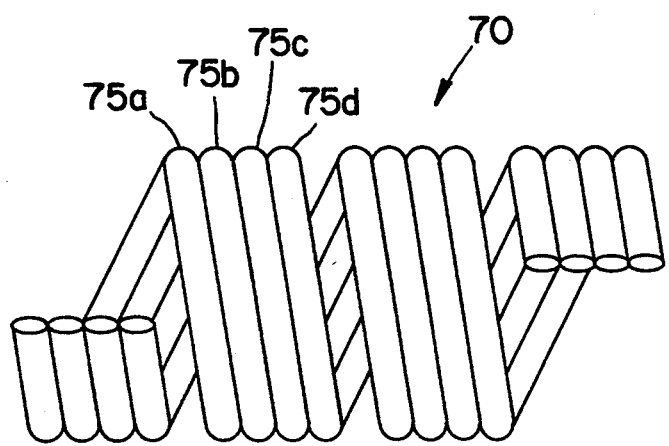
FIG. 2b is a side elevational view of a quadrafilar conductor winding for use in a lead conductor.

Referring now to the drawings, FIG. 1 shows a lead system 10 which includes a lead assembly 15, an anchoring sleeve 20, a connector 25, a stylet guide 30, and a stiffening stylet 35. Referring now to FIG. 1a, the lead assembly 15 is shown in greater detail with an electrode structure 40 at a distal end of the lead assembly 15, a tine 45 to secure the lead assembly 15 endocardially, a lead conductor 50 in a multifilar coil configuration which allows the stiffening stylet 35 to be inserted into the lead assembly 15 in the internal lumen 52 of the lead conductor 50. The lead conductor 50 is shown attached at its distal end 55 to the electrode structure 40. The lead conductor 50 is also similarly attached at a proximal end (not shown) to the connector 25. Multifilar coil configurations are also shown in FIGS. 2a and 2b in a trifilar 60 coil configuration having individual wires 65a, 65b and 65c and a quadrafilar 70 coil configuration having individual wires 75a, 75b, 75c, and 75d. Insulation elements 57a, 57b and 57c insulate portions of the electrode structure 40 and the lead conductor 50. Such insulation elements 57a, 57b, and 57c may be made from conventional silicone and polyurethane lead insulation materials. While a unipolar lead is shown, and described above, the present invention can also be applied to bipolar leads in the same manner. As used in implantable pacing leads, the individual wires of the lead conductor would be typically about 0.004 to 0.010 in diameter and would be wound into extremely small coils; typically having a diameter of less than 2–3 mm.

Coiling of the duplex alloy wire to make medical leads is nearly identical to that employed in making multifilar MP35N coils except that the differences in modulus and strength dictate the use of different mandrel size and wire tension settings that will be readily appreciated by those skilled in the art. Incorporation of the duplex multifilar coil into a final lead assembly could involve welding to the connector and electrode materials since the materials presently used for those elements are materials to which the duplex stainless steel is generally weldable or it could involve crimping the coil onto electrode and connector elements. In multiconductor electrodes, the wires may be provided individually with a polymeric insulation material such as silicone, polyurethane, PTFE, ETFE, polyethylene, polypropylene and other polymer coatings which can be applied by conventional means.

EXAMPLES

Selected corrosion-resistant alloys were investigated for potential use in pacemaker lead applications. The mechanical, corrosion and MIO characteristics of each of these alloys was characterized and compared to those of conventional lead conductor materials, including MP35N, 316L stainless steel, 304L stainless steel and Elgiloy. Quadrafilar coils 0.030 inch in diameter were made from 0.005 inch diameter wire by conventional coil winding methods. The coils were subjected to coil bending fatigue tests which consisted of reverse bending of the coils about a fixed radius of curvature (i.e. at 0.084 inch and at 0.118 inch) and recording the number of cycles required to induce coil fracture. The results are as set forth in Table 1.

TABLE 1

| Alloy | Tensile Strength (KPSI) | Cycles r = 0.084" | Cycles r = 0.118" |
|---|---|---|---|
| MP35N | 290 | 14500 | 65000 |
| 316LVM | 254 | 15900 | 34100 |
| 316LVM | 239 | 14500 | 23500 |
| 316LVM | 221 | 11100 | 18600 |
| 316LVM | 186 | 9400 | 16300 |
| Elgiloy | 269 | 22600 | 59900 |
| 304LVM | 337 | 58700 | 250000 |
| 304LVM | 300 | 88600 | >1000000 |
| 304LVM | 268 | 60600 | 500000 |
| 304LVM | 246 | 27200 | 78800 |
| SA2507 | 286 | 19800 | 147300 |

The tendency of each coil material to produce metal ion oxidation (MIO) in polymers was tested in an accelerated in vitro screening test by placing the metal conductor coils into an insulator tube of the polyether urethane Pellethane 80A, tying the ends of the tube and placing the assembly in an aqueous oxidizing solution. The test sample was then stored in the test solution at 37° C. with the test solution changed three times per week. Control tubing which contained no conductor coil was used for comparison. At the end of 90 days, the qualitative visual condition of the tubing was noted (i.e. inspection for cracks characteristic of MIO) and the ultimate tensile strength and elongation at break of the tubing were measured. The results of the test were as set forth in Table 2.

TABLE 2

| Alloy | Visual | Tensile Strength (PSI) | Elongation (%) |
|---|---|---|---|
| Control | clear | 11090 | 540 |
| MP35N | cracks | 3700 | 470 |
| Elgiloy | cracks | 12600 | 570 |
| 316LVM* | clear | 5730 | 520 |
| 304LVM* | clear | 5730 | 520 |
| SA2507 | clear | 13100 | 575 |

*Different tubing lot: Control 9188 PSI/505%

Corrosion resistance testing was conducted according to electrochemical anodic polarization techniques to determine the corrosion rate, metastable pitting, and pitting potential, in the potential range used in implantable medical device applications. The results are shown in Table 3.

TABLE 3

| Alloy | Observed Result |
|---|---|
| Elgiloy | No corrosion pitting |
| MP35N | No corrosion pitting |
| 316LVM | Pitting excursions |
| 304LVM | Pitting excursions |
| SA2507 | No corrosion |

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A medical electrical lead comprising:
   (a) an electrode at a distal end thereof;
   (b) a connector at a proximal end thereof; and
   (c) an elongated electrical conductor extending between the electrode and the connector, the conductor in electrical contact with the electrode at a distal end and in electrical contact with the connector at a proximal end, the conductor comprised of a wire wound in a coil configuration, the wire comprised of a duplex stainless steel having a composition of at least 22% chromium, at least 3% molybdenum and at least 5% nickel.

2. The medical electrical lead of claim 1 wherein the coil configuration is a plurality of wires in a multifilar coil configuration.

3. The medical electrical lead of claim 1 wherein the duplex stainless steel has a nominal composition of Fe—25Cr—7Ni—4Mo—0.3N.

4. A medical electrical lead comprising:
   (a) an electrode at a distal end thereof;
   (b) a connector at a proximal end thereof;
   (c) a hollow polymeric insulator extending between the proximal and distal ends, said polymeric insulator comprising a material susceptible to metal ion oxidative degradation; and
   (d) an elongated electrical conductor within the polymeric insulator and extending between the electrode and the connector, the conductor in electrical contact with the electrode at a distal end and in electrical contact with the connector at a proximal end, the conductor comprised of a wire wound in a coil configuration, the wire comprised of a duplex stainless steel having a composition of at least 22% chromium, at least 3% molybdenum and at least 5% nickel.

5. The medical electrical lead of claim 4 wherein the coil configuration is a plurality of wires in a multifilar coil configuration.

6. The medical electrical lead of claim 4 wherein the duplex stainless steel has a nominal composition of Fe—25Cr—7Ni—4Mo—0.3N.

* * * * *